United States Patent [19]

Ganguly

[11] Patent Number: 4,656,035
[45] Date of Patent: Apr. 7, 1987

[54] METHOD OF SEPARATING BLOOD PLATELETS

[75] Inventor: Pankaj Ganguly, Memphis, Tenn.

[73] Assignee: University of Tennessee Research Corporation, Knoxville, Tenn.

[21] Appl. No.: 685,245

[22] Filed: Dec. 21, 1984

[51] Int. Cl.$^4$ ............................................. A61K 35/14
[52] U.S. Cl. ............................................. 424/101; 435/2
[58] Field of Search ............................ 435/2; 424/101

[56] References Cited

PUBLICATIONS

Williams et al–Hematology–2nd edit. (1977), pp. 1176 and 1187.
Patscheke et al–Chem. Abst. vol. 86 (1977), p. 169,192a.
Kinae et al–Chem. Abst. vol. 92 (1980), p. 56730e.

*Primary Examiner*—Sam Rosen
*Attorney, Agent, or Firm*—Ronald L. Lyons

[57] ABSTRACT

A method of obtaining young blood platelets is disclosed which comprises adding at least one lectin to a mixture of blood platelets allowing this mixture to agglutinate, isolating the agglutinated product, and then removing the young agglutinated platelets from the lectin. This results in a composition consisting essentially of young blood platelets.

13 Claims, No Drawings

METHOD OF SEPARATING BLOOD PLATELETS

BACKGROUND OF THE INVENTION

1. Field of the Invention

A method of separating young blood platelets from a mixture of young and old blood platelets is disclosed. The method comprises adding a lectin under nonactivating conditions to a mixture of young and old blood platelets and allowing agglutination. The agglutinated young blood platelets may be isolated from the older blood platelets and then separated from the lectin. This results in a composition consisting essentially of young blood platelets.

2. Description of the Prior Art

Platelets are small cells in human or animal blood which are essential for the clotting of blood. Platelets in circulation in the body are a heterogeneous mixture of platelets of different ages. Platelets are very fragile and when stored in a blood bank are usually discarded after approximately 4 days because of age. Age becomes apparent because of the loss of platelet functionality and metabolic capabilities. Further, when platelets are used from a blood bank only about one half of the platelets survive in circulation. As mentioned, it is known that younger platelets have higher metabolic and functional capabilities as compared to older platelets. In addition to the above mentioned advantages, younger platelets have a longer shelf life than currently used blood platelet mixtures which contain both young and old blood platelets. Therefore, a need arose to devise a gentle method of selectively isolating the younger platelets from a platelet mixture of different ages.

Ganguly et al; *Biochem. Biophys. Res. Comm.*, 1979, 89(4), 1154–1160, discloses that wheat germ agglutinin binds to the surface of human platelets and leads to their agglutination. Wheat germ agglutinin caused clumping of fresh platelets. It is further disclosed that in washed human platelets, wheat germ agglutinin is known to bind to surface glycoproteins and thereby induce cell agglutination.

*Chemical Abstracts* 92: 56730e discloses that three lectins separated from *Ulex europius, Ricinus communis,* and *Glycine max* (soybean) induce aggregation of human platelets.

Greenberg et al; *Biochim. Biophys. Acta,* 1974, 345, 231–242 discloses that out of nine lectins studied, wheat germ agglutinin was the most effective towards platelet aggregation.

Naim et al; *Thrombosis Res.*, 1982, 26, 431–441 discloses that lectins are useful for the isolation of glycoproteins because they have pronounced affinities for certain sugars.

Lectins are known to cause human blood platelet agglutination (aggregation) by binding to surface glycoproteins. Wheat germ agglutinin is especially known to be an effective agglutinator. Lectins are also used to isolate glycoproteins because of their affinity for specific sugars. However, the instant invention is novel and certainly an advancement in the art in that (1) lectins are used to separate platelets depending on the number of surface sugars present and (2) blood platelets have fewer surface sugars as the platelets become older. Therefore, in the instant invention young blood platelets are obtained by adding to a mixture of blood platelets at least one lectin; allowing the blood platelet mixture containing the lectin to agglutinate; isolating the agglutinated product and then removing the lectin from the agglutinated product resulting in a composition consisting essentially of young blood platelets.

BRIEF SUMMARY OF THE INVENTION

An object of this invention is to provide a method of obtaining young blood platelets from a mixture of young and old blood platelets.

Another object of this invention is to prepare a composition consisting essentially of young blood platelets.

Another object of this invention is to provide a method which will differentiate between young blood platelets and older blood platelets by the difference in the number of sugars on the surface of the platelets.

Another object of this invention is to provide a method of separating young blood platelets which contain larger numbers of surface sugars from older blood platelets which contain fewer surface sugars.

As is known, blood platelets are small cells in blood which are essential to blood clotting. Young blood platelets are more functional and have a longer shelf life than currently used blood platelet mixtures which contain both young and old blood platelets. Also, young blood platelets have a greater number of sugar groups on their surface than old blood platelets. Lectins bind to specific sugar groups. Therefore, lectins are used in the instant invention to promote preferential agglutination of young blood platelets from a blood platelet mixture. Whereby the agglutinated young blood platelets are separated from the non-agglutinated old blood platelets. Then the agglutinated young blood platelets are separated or released from the lectin by washing them with a sugar which removes the lectin and provides an isolated composition of young blood platelets.

DESCRIPTION OF PREFERRED EMBODIMENTS

A sufficient amount of lectin to cause agglutination of young blood platelets is added to a mixture of young and old blood platelets. The lectins are used to separate or differentiate between any two blood platelets by the number of sugars on the surface of the platelets. As mentioned, older blood platelets have fewer surface sugars than the younger blood platelets. The agglutinated young blood platelets are separated from the non-agglutinated older blood platelets after which the agglutinated young blood platelets are released from the lectin by contacting the agglutinated young blood platelets and lectin with a sugar. The lectins preferred herein are non-activating lectin. When the term nonactivating lectin is used herein it is meant to mean that under the conditions of these experiments, the lectin does not cause gross and irreversible alterations of platelets resulting in their aggregation and secretion of granular contents.

Human platelets survive in circulation for about a week. When the term young blood platelet is used herein it is meant to mean platelets which have recently been produced from its precursor cells, the megakaryocytes, and are likely to remain functional and in circulation longer than the older platelets.

When the term old blood platelet is used herein it is meant to mean platelets which have been in circulation for a number of days, have lost some of its surface sugars and are likely to remain in circulation for a time shorter than the younger platelets.

The preferred amount of lectin used to cause agglutination of young blood platelets in a mixture of young and old blood platelets is from about 50 μg to about 100 μg lectin per ml of said mixture.

The younger blood platelets have about 4.31 PAS units of sugar containing surface proteins compared to 1.50 PAS units for the older blood platelets.

Thus, the younger platelets have approximately three times more surface glycoproteins than the older platelets.

The preferred temperature for allowing the blood platelet mixture and lectin to agglutinate is from about 20° C. to about 37° C.

The preferred method of isolating the agglutinated young blood platelets from the old blood platelets is sedimentation under unit gravity.

The preferred method of removing the lectin from the agglutinated young blood platelets is contacting the lectin and agglutinated young blood platelets with a sufficient amount of sugar to cause dissociation of the lectin and the young blood platelets.

The preferred contacting step is a resuspension and washing step where the lectin and agglutinated young blood platelets are washed with a sugar. The sugar is preferably selected after knowing the specificity of the lectin being employed. The most preferred sugars are N-acetylglucosamine and α-methyl-D-mannoside.

The preferred lectin is selected from the group consisting of wheat germ agglutinin, soybean lectin, *Ricinus communis*, *Aquaricus bisporus*, concanavalin A, *Lathorus sativus*, *Pisum sativum*, peanut agglutinin and lentil lectin. The most preferred lectins are wheat germ agglutinin and lentil lectin. When using wheat germ agglutinin it is preferred to use N-acetylglucosamine as the sugar and when using lentil lectin it is preferred to use α-methyl-D-mannoside.

The amount of lectin added is from 30 μg/ml to about 150 μg/ml. The preferred amount of lectin added is from 50 μg/ml to about 100 μg/ml.

A composition consisting essentially of young blood platelets may be prepared by the above described process.

EXAMPLE 1

Separation of a Heterogeneous Platelet Population Into Two Fractions 9 parts of human blood is drawn into a plastic syringe containing 1 part of 3.8% trisodium citrate. Blood from both humans, rabbits and other animals may be used.

The mixture of blood and trisodium citrate is centrifuged in an IEC clinical centrifuge at room temperature for a period of 3 minutes each at 2000 rpm. The blood is contained in conical plastic tubes. Each tube has a 15 ml capacity. After each centrifuged period, the platelet-rich plasma (PRP) is removed from the top and the remaining blood is spun again. Depending on the donor, three periods of such centrifugation may yield a total volume of PRP of about 40% of the starting volume of blood.

Then 0.1 parts of a 0.1M ethylene diamine tetracetate (sodium EDTA) solution is added to the PRP. The mixture is mixed well by inverting the plastic tubes and then these are centrifuged by the above described procedure for a period of 10 to 15 minutes. The platelets sediment to the bottom of the tube and the supernatant is then removed. The platelets may be resuspended in Tris (25 mM)-saline (125 mN NaCl), pH 7.4 containing 3% human serum albumin at a cell count of 3.0 to $4.0 \times 10^8$/ml.

A solution of wheat germ agglutinin (WGA) in Tris-saline buffer is prepared. The WGA may be obtained from U.S. Biochemicals, Cleveland, Ohio. The following amounts of WGA, 0 (control), 20, 30, 40, 50, 60, 70 and 80 μg/ml of the platelet suspension is placed in clean, conical plastic tubes held vertically in a test tube rack. All volumes are adjusted the same with Tris-buffered saline.

An aliquot of the platelet suspension is then added to the WGA solution in each tube. The tubes are capped and the contents rapidly but gently mixed by inversion. The samples are examined from time to time. Part of the platelets in the tubes clump together and fall to the bottom of the tube.

The platelets in suspension are collected with a plastic pipet in a plastic tube. The agglutinated platelets are resuspended in Tris-buffered saline containing albumin. N-acetylglucosamine is added to both platelet samples to a final concentration of 50 mM. The tubes are kept at room temperature for 10 minutes. The sugar displaces the lectin from the cells, the agglutinated cells dissociate and go back into suspension.

The cell suspensions are diluted with Tris-buffered saline and the platelets are collected by centrifugation. The supernatants containing the free lectin are discarded. Depending on the need, the separated platelet populations may be washed and resuspended in a suitable medium.

Quantitative measurements show that older platelets have much less glycoproteins, and probably glycolipids, than younger platelets. Since lectins recognize and specifically interact with sugar-containing surface groups, the agglutinated and less-agglutinated platelet fractions that are isolated represent young and old platelet populations. The optimal lectin concentration deduced from this experiment is about 90 μg/ml and the optimal time of incubation is about 50 minutes.

EXAMPLE II

Lectin Fractionation of Platelets

Rabbit blood platelets suspended in 25 mM Tris-125 mM NaCl, pH 7.4 plus 3% bovine serum albumin are incubated with 60 to 90 μg/ml concentration of WGA for 45 to 60 minutes time at room temperature. The platelets are partially agglutinated and the agglutinated cells settle to the bottom of the tube leaving the other platelets in the top. The clearing at the top of the samples will contain very few platelets. The less agglutinated cells in the top may be carefully removed with a plastic pipet. The agglutinated cells are resuspended in Tris-buffered saline containing 50 mM N-acetylglucosamine and both cell fractions are washed once in the presence of the sugar. Approximately 40% of the initial platelets are in the agglutinated fraction while 60% are in the less-agglutinated part.

We claim:

1. A method of separating young blood platelets from a mixture of young and old blood platelets comprising:
    (a) adding a sufficient amount of lectin to cause agglutination of blood platelets to a mixture of young and old blood platelets;
    (b) allowing the blood platelet mixture and lectin to agglutinate;
    (c) isolating the agglutinated young blood platelets from the old blood platelets; and
    (d) removing the lectin from said agglutinated young blood platelets.

2. The method according to claim 1 wherein the lectin is selected from the group consisting of wheat germ agglutinin, soybean lectin, *Ricinus communis, Aqaricus bisporus,* concanavalin A, *Lathvrus sativus, Pisum sativum,* peanut agglutinin and lentil lectin.

3. The method according to claim 2 wherein the lectin is wheat germ agglutinin.

4. The method according to claim 2 wherein the lectin is lentil lectin.

5. The method according to claim 1 wherein the lectin is non-activating.

6. The method according to claim 1 wherein the amount of lectin added is from 30 μg/ml to about 150 μg/ml.

7. The method according to claim 5 wherein the amount of lectin added is from 80 μg/ml to about 100 μg/ml.

8. The method according to claim 1 wherein a sugar is added in step (d) in sufficient amounts to cause dissociation of the lectin and young blood platelets resulting in the lectin being removed from the agglutinated young blood platelets.

9. The method according to claim 8 wherein step (d) comprises removing the lectin from the agglutinated young blood platelets by resuspension and washing the mixture with sugar.

10. The method according to claim 7 wherein the lectin is wheat germ agglutinin.

11. The method according to claim 9 wherein the sugar is N-acetylglucosamine.

12. The method according to claim 7 wherein the lectin is lentil lectin.

13. The method according to claim 12 wherein the sugar is α-methyl-D-mannoside.

* * * * *